United States Patent [19]

Engelhardt et al.

[11] 4,258,211

[45] Mar. 24, 1981

[54] 4-AMINOALIPHATIC-2,3,5,6-[DIBENZOBICYCLO[5.1.0]OCTANES] AND SALTS THEREOF

[75] Inventors: Edward L. Engelhardt, Gwynedd Valley; David C. Remy, North Wales, both of Pa.

[73] Assignee: Merck & Co., Inc., Rahway, N.J.

[21] Appl. No.: 310,188

[22] Filed: Nov. 28, 1972

Related U.S. Application Data

[63] Continuation-in-part of Ser. No. 93,494, Nov. 27, 1970, abandoned, and Ser. No. 59,671, Jul. 30, 1970, abandoned, which is a continuation-in-part of Ser. No. 662,882, Aug. 24, 1967, abandoned, said Ser. No. 93,494, is a continuation-in-part of Ser. No. 834,601, Jun. 9, 1969, abandoned, which is a continuation of Ser. No. 662,881, Aug. 24, 1967, abandoned.

[51] Int. Cl.$^3$ .............................................. C07C 87/28
[52] U.S. Cl. .................................. 564/379; 260/501.1; 260/501.18; 424/316; 424/330; 564/380
[58] Field of Search .............. 260/570.8 TC, 590, 649, 260/618, 570.8

[56] References Cited

U.S. PATENT DOCUMENTS

| | | | |
|---|---|---|---|
| 3,547,933 | 12/1970 | Coyne et al. | 260/570.8 X |
| 3,574,199 | 4/1971 | Coyne et al. | 260/570.8 X |

*Primary Examiner*—Robert V. Hines
*Attorney, Agent, or Firm*—William H. Nicholson; Harry E. Westlake, Jr.

[57] ABSTRACT

This invention concerns 2,3,5,6-dibenzobicyclo[5.1.0]octanes which may be substituted at the 4-position by either halogen, ketonic oxygen or hydroxyl. These compounds are prepared from 5H-dibenzo[a,d]cyclohepten-5-one by reaction with ethyl trichloroacetate in the presence of sodium methoxide to give 8,8-dichloro-2,3,5,6-dibenzobicyclo[5.1.0]octan-4-one which is reduced to the corresponding 4-hydroxy compound. The resulting 4-hydroxy compound is dehalogenated and converted to the corresponding 4-chloro or 4-keto compound. The 4-substituted compounds are useful in preparing other compounds of our invention.

4-Dialkylaminopropylidenedibenzobicyclo[5.1.0]octane compounds and 4-dialkylaminopropyldibenzobicyclo[5.1.0]octane compounds, useful as antidepressant agents, are prepared from, respectively, dibenzobicyclo[5.1.0]octan-4-one by reaction with a dialkylaminopropyl Grignard reagent followed by dehydration of the resulting carbinol or by reaction of a 4-halo-2,3,5,6-dibenzobicyclo[5.1.0]octane with a dialkylaminopropyl Grignard reagent. Both the dialkylaminopropyl and the dialkylaminopropylidene compounds are converted to the corresponding monoalkylamino compounds by dealkylation.

16 Claims, No Drawings

4-AMINOALIPHATIC-2,3,5,6-[DIBENZOBICYCLO[5.1.0]OCTANES] AND SALTS THEREOF

The present application is a continuation-in-part of application Ser. No. 93,494, filed Nov. 27, 1970 and now abandoned, which in turn is a continuation-in-part of application Ser. No. 834,601, filed June 9, 1969 and now abandoned, which in turn is a continuation of application Ser. No. 662,881, filed Aug. 24, 1967, and now abandoned, of Edward L. Engelhardt and David C. Remy. The present application is also a continuation-in-part of application Ser. No. 59,671, filed July 30, 1970, and now abandoned which in turn is a continuation-in-part of application Ser. No. 662,882, filed Aug. 24, 1967 and now abandoned, of Edward L. Engelhardt and David C. Remy.

This invention relates to certain 2,3,5,6-dibenzobicyclo[5.1.0]octane compounds which contain a reactive substituent at the 4-position represented by the following structural formula:

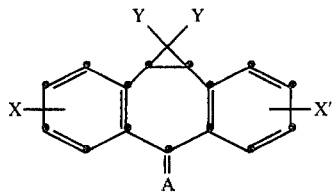

wherein
Y is hydrogen or halogen (especially chlorine or bromine),
A is a bivalent substituent or two monovalent substituents consisting of 2 hydrogens, a hydrogen and halogen, ketonic oxygen or hydrogen and hydroxyl, and
X and X' are either similar or dissimilar and are selected from the group consisting of hydrogen, lower alkyl, lower alkoxy, phenyl or substituted phenyl, acyl having up to 4 carbon atoms, lower alkylsulfonamido, hydroxyl, carboxy, carbamoyloxy, lower alkylcarbamoyloxy, dilower alkylcarbamoyloxy, lower alkoxycarbamoyloxy, mercapto, lower alkylmercapto, lower alkylsulfonyl, lower alkylsulfamoyl and dilower alkylsulfamoyl.

An especially preferred group of 2,3,5,6-dibenzobicylo-[5.1.0]octane compounds are compounds of the above type wherein X and X' are selected from hydrogen, lower alkyl, lower alkoxy, phenyl or substituted phenyl, hydroxyl, carboxy, mercapto, lower alkylmercapto, lower alkylsulfonyl and sulfamoyl. The present invention also includes the process for the preparation of the dibenzobicyclo-[5.1.0]octane compounds and to certain intermediates prepared in the course of such preparation.

This invention also relates to certain 2,3,5,6-dibenzobicyclo[5.1.0]octane compounds exemplified by the following structural formulae:

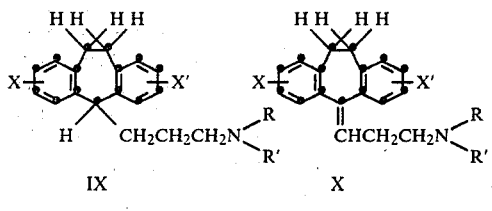

wherein
R' is either hydrogen or lower alkyl and
R is lower alkyl,
X and X' are either similar or dissimilar and are selected from the group consisting of hydrogen, lower alkyl, lower alkoxy, phenyl or substituted phenyl, hydroxyl, carboxy, mercapto, lower alkylmercapto, lower alkylsulfonyl, sulfamoyl, lower alkylsulfamoyl, and dilower alkylsulfamoyl.

This invention also includes the process for the preparation of the final products and synthesis of intermediates used in the preparation of the products.

These new 4-substituted dibenzobicyclo[5.1.0]octane compounds are useful as intermediates in the process for preparing certain pharmaceuticals. Thus, the 4-chlorodibenzobicyclo[5.1.0]octane compound is utilized in the preparation of 4-(3-dimethylaminopropyl)-2,3,5,6-dibenzobicyclo[5.1.0]octane which is useful in the treatment of depression. The 4-chloro compound is condensed with 3-dimethylaminopropylmagnesium chloride to produce the desired 4-dimethylaminopropyl substituted dibenzobicyclo[5.1.0]octane compound which is demethylated to produce the corresponding N-monomethylaminopropyl compound. The 4-keto intermediate is used in the preparation of other compounds by reaction of the 4-keto compound with a dialkylaminopropylmagnesium chloride followed by hydrolysis of the resulting Grignard adduct to produce the corresponding 4-hydroxy-4-(3-dimethylaminopropyl) derivative which can then be dehydrated to produce 4-(3-dimethylaminopropylidene)-2,3,5,6-dibenzobicyclo[5.1.0]octane which is useful in the treatment of depression. The intermediates of the subject application therefore are useful in the preparation of 4-(3-dimethylaminopropyl)-2,3,5,6-dibenzobicyclo[5.1.0]octane and/or 3-(dimethylaminopropylidene)-2,3,5,6-dibenzobicyclo[5.1.0]octane which are useful in the treatment of mental disorders because of their antidepressant activity. This antidepressant activity is evidenced in animal tests in mice sedated with tetrabenazine. Thus, in mice the sedative action of tetrabenazine is reversed by the administration of either of the above-named compounds.

The compounds are conveniently administered in the form of their acid addition salts with non-toxic, pharmaceutically acceptable acids and these salts are also included in the scope of this present invention. They are administered in an amount of from 1-200 mg./dose to be administered 2-4 times/day.

These active new pharmaceuticals are also disclosed and claimed in U.S. application Ser. No. 59,671, filed July 30, 1970, which is a continuation-in-part of U.S. application Ser. No. 662,882, filed Aug. 24, 1967, and now abandoned.

In carrying out the process of the present invention as illustrated in the following flow sheet 5H-dibenzo[a,d]cyclohepten-5-one or a derivative thereof containing an additional substituent in one or both of the benzenoid rings is treated with dichlorocarbene, generated for example, from ethyl trichloroacetate in the presence of sodium methoxide, to give 8,8-dichloro-2,3,5,6-dibenzobicyclo[5.1.0]octan-4-one which in turn is reduced with an alkali metal borohydride to the corresponding 4-hydroxy compound III hereinbelow. The resulting 4-hydroxy-8,8-dichloro compound is converted to the corresponding dehalogenated compound by reduction with lithium and t-butyl alcohol to produce compound IV as illustrated hereinbelow. This key intermediate may then be converted by appropriate reactions to the corresponding 4-chloro or 4-keto compound. The 4-keto-2,3,5,6-dibenzobicyclo[5.1.0]octane compound is reduced using a variant of the Wolf-Kishner reaction to the corresponding 2,3,5,6-dibenzobicyclo[5.1.0]octane compound VII in the flow sheet.

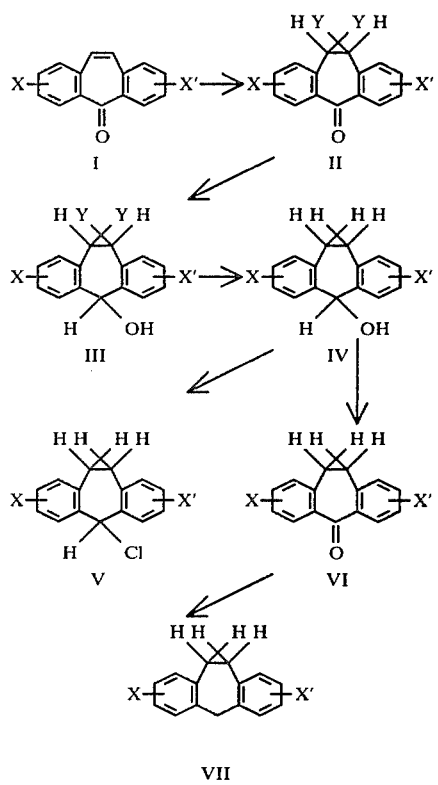

wherein X, X' and Y are as previously defined. In accordance with one embodiment of the process of our invention a 5H-dibenzo[a,d]cyclohepten-5-one or a derivative which contains one or more additional substituents in the benzenoid ring is contacted with a dihalocarbene in solution under strongly alkaline reaction conditions, e.g., ethyl trichloroacetate in the presence of sodium methoxide to produce an 8,8-dichloro-2,3,5,6-dibenzobicyclo[5.1.0]octan-4-one (II).

The 4-ketone produced is then reduced with an alkali metal borohydride to produce the corresponding 4-hydroxy compound 8,8-dihalo-2,3,5,6-dibenzobicyclo-[5.1.0]octan-4-ol (III) hereinabove. The thus-obtained 4-hydroxy-8,8-dihalo compound is dehalogenated by reducing with an alkali metal in a lower alkanol, as for example, t-butyl alcohol to produce 2,3,5,6-dibenzobicyclo[5.1.0]octan-4-ol compound (IV) hereinabove. This key intermediate may then be converted by utilization of appropriate reaction conditions to the corresponding 4-halo or 4-keto compound. In producing the 4-halo compound, as for example, the 4-halo-2,3,5,6-dibenzobicyclo[5.1.0]-octane, the above-mentioned 4-hydroxy compound IV is treated with, for example, dry hydrogen chloride to produce the corresponding 4-chloro-2,3,5,6-dibenzobicyclo[5.1.0]octane. Alternatively, the 4-hydroxy compound IV is converted to the 4-keto compound VI by oxidation with chromium trioxide in sulfuric acid. The 2,3,5,6-dibenzobicyclo[5.1.-0]octane, compound VII hereinabove, is obtained by reduction of the corresponding 4-keto compound using hydrazine in a variant of the Wolf-Kishner reaction. As indicated, each of these compounds IV, V, VI and VII are useful as intermediates in the preparation of valuable pharmaceuticals.

As indicated above, the first step in the reaction sequence outlined in the flow sheet, i.e., the introduction of the cyclopropane substituent at the 10,11-position of the dibenzocycloheptene molecule is effected by treating a 5H-dibenzo[a,d]cyclohepten-5-one with a source of dichlorocarbene. A common method of producing dichlorocarbene is by contacting a compound such as trichloroacetic acid, a lower alkyl ester or chloroform with a strong base as, for example, with an alkali metal alkoxide such as sodium or potassium alkoxide. The unsaturated ketone 5H-dibenzo[a,d]cycloheptenone is mixed in solution with ethyl trichloroacetate and sodium methoxide and the formed dichlorocarbene adds to the 10,11-double bond producing the desired dibenzobicyclooctane compound having chloro substituents attached to the 8-position. The dichloro ketone is readily recovered as a solid by recrystallization from methanol.

The next step in the reaction sequence is the selective reduction of the 4-keto compound to the corresponding 4-hydroxy compound by use of an alkali metal borohydride such as sodium, potassium or lithium borohydride. In this reduction reaction the ketone is mixed in solution with an excess of the alkali metal borohydride. The reaction is preferably conducted in an inert organic solvent for the compound such as a lower alkanol or ether. The resulting 4-hydroxy compound is then dehalogenated by reduction under conditions which will remove the halogen from the molecule without effecting any other rearrangements. One method for carrying out the dehalogenation is to dissolve the 4-hydroxy-8,8-dichloro-2,3,5,6-dibenzobicyclo[5.1.0]octane in an alcohol and add thereto a suitable amount of an alkali metal thereby removing the halogen substituents from the molecule to produce the 4-hydroxy-2,3,5,6-dibenzobicyclo[5.1.0]octane compound. Thus, for example, in a preferred method of carrying out this step of the invention 8,8-dichloro-2,3,5,6-dibenzobicyclo[5.1.0]-octan-4-ol is reduced in solution in a lower alkanol to the corresponding dehalogenated compound by heating said compound in a mixture of lithium and t-butyl alcohol to produce 2,3,5,6-dibenzobicyclo[5.1.-0]octan-4-ol. The resulting dechlorinated alcohol is then conveniently converted to the corresponding 4-chloro compound by treatment with a reagent such as dry hydrogen chloride, phosphorus trichloride and the like.

The 2,3,5,6-dibenzobicyclo[5.1.0]octan-4-ol is then oxidized to produce the corresponding 4-keto compound by treatment of said 4-ol with chromium trioxide under acid conditions.

As illustrated in the following flow sheet showing the preparation of the compounds of our invention, the 4-dialkylaminopropylidenedibenzobicyclo[5.1.0]octane compounds are prepared from the starting dibenzobicyclo[5.1.0]octan-4-one by reaction under anhydrous conditions with 3-dialkylaminopropylmagnesium chloride. The Grignard adduct initially formed as a result of the Grignard reaction is hydrolyzed to produce the resulting tertiary carbinol, i.e., 4-hydroxy-4-(3-dialkylaminopropyl)-2,3,5,6-dibenzobicyclo[5.1.0]octane. The carbinol formed in this manner is then treated with a dehydrating agent and heated to split out the hydroxyl substituent at the 4-position and produce the resulting bicyclo[5.1.0]octane compound, i.e., 4-(3-dialkylaminopropylidene)-2,3,5,6-dibenzobicyclo[5.1.0]octane.

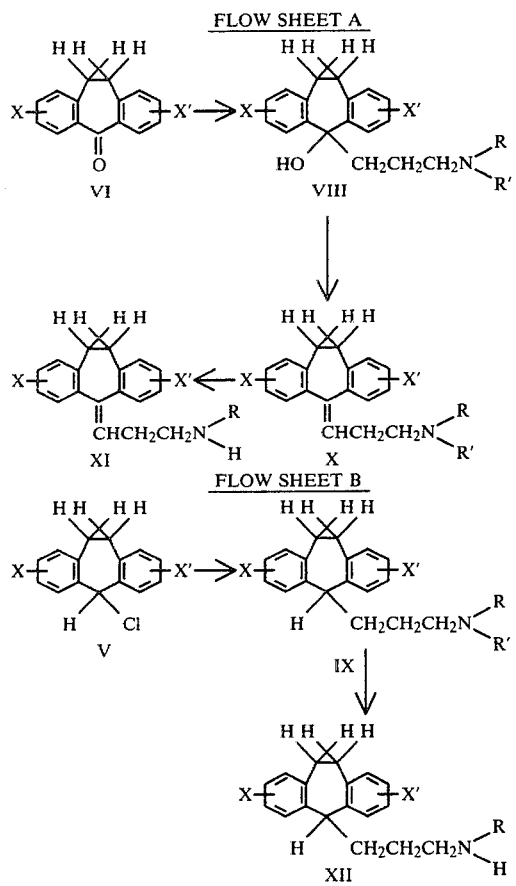

The corresponding alkylaminopropyl derivatives, compound XII hereinabove, are prepared by the process starting from the corresponding 4-halo e.g., 4-chloro compound, the preparation of which is described in application Case No. 11337, U.S. application Ser. No. 662,881, filed Aug. 24, 1967, of Edward L. Engelhardt and David C. Remy, now abandoned. In carrying out the first step of the reaction in this process for the preparation of the alkylaminopropyl compounds, the Grignard reagent prepared from 3-dialkylaminopropyl chloride is condensed with 4-halo-2,3,5,6-dibenzobicyclo[5.1.0]octane in a dry solvent to produce the 4-(3-alkylaminopropyl)-2,3,5,6-dibenzobicyclo[5.1.0]octane. These processes are illustrative of methods of producing the dialkylaminopropyl or propylidene derivatives of the compounds of the present invention.

The corresponding monoalkylaminopropyl or propylidene compounds may be produced by reaction of the tertiary aminopropyl or propylidene compound with a haloformate or halothioformate to produce the corresponding urethane or thiourethane intermediate.

The urethane intermediate thus produced is then subjected to hydrolysis to produce the corresponding secondary amine. The hydrolysis is preferably carried out under basic conditions. A preferred method for producing the corresponding monoalkylaminopropyl or propylidene compounds from the dialkylaminopropyl or propylidene compounds is to condense the tertiary aminopropyl or propylidene compound with 2-tolysulfonylethylchloroformate to produce the corresponding urethane intermediate. The urethane derivative thus produced is subjected to mild hydrolysis to produce the corresponding secondary amine. The examples which follow are merely illustrative of the compounds of the present invention and are not intended to be restricted thereto. The new compounds of the present invention are obtained as a mixture of geometric isomers or as individual isomers. The geometric isomers, when isolated in their pure form, may differ in biological activity.

EXAMPLE 1

8,8-DICHLORO-2,3,5,6-DIBENZOBICYCLO[5.1.0]OCTAN-4-ONE

Into a flame-dried, nitrogen-flushed 500 ml. round-bottom flask, provided with dropping funnel, stirrer, and condenser with calcium chloride drying tube, was placed 5H-dibenzo[a,d]cyclohepten-5-one (20.52 g., 0.1 mole), sodium methoxide (50 g., 0.925 mole) and 150 ml. of dry benzene. The mixture was stirred and cooled in an ice bath. Ethyl trichloroacetate (165 g., 0.85 mole) was added dropwise over a 3 to 4 hour period while stirring vigorously. After the addition had been completed, the mixture was stirred an additional 5 hours at 0° C. and then overnight at room temperature. Water (150 ml.) was added to hydrolyze the mixture. The benzene phase and a benzene extract of the aqueous phase were combined and the solvent was removed under reduced pressure on the steam bath. Trituration of the deep brown residue induced rapid crystallization. The solid product was collected and washed with cold methanol. Recrystallization from methanol gave 17.56 g. (61%) of product, m.p. 132°–133° C. An analytical sample melted at 132°–134° C. after recrystallization from methanol.

Analysis Calc'd. for $C_{16}H_{10}Cl_2O$: C, 66.45; H, 3.49; Cl, 24.52. Found: C, 66.14; H, 3.49; Cl, 24.39.

EXAMPLE 2

8,8-DICHLORO-2,3,5,6-DIBENZOBICYCLO[5.1.0]OCTAN-4-OL 8,8-Dichloro-2,3,5,6-dibenzobicyclo[5.1.0]octan-4-one (I) (2.00 gm., 6.93 mmole) was dissolved in 40 ml. of hot methanol. The solution was stirred while a solution of 0.941 gm. (17.5 mmole) of potassium borohydride in 10 ml. of water (containing 2 drops of 40% sodium hydroxide solution) was added dropwise over a 15 minute period. The clear solution was refluxed for 1.5 hours. After evaporation of the methanol in vacuo, a white crystalline mass remained. After cooling in an ice bath, the product was collected, washed with water and dried. Recrystallization from aqueous methanol gave 1.51 gm. (75%) of product, m.p. 170.5°–172.5°.

Analysis Calc'd. for $C_{16}H_{12}OCl_2$: C, 66.00; H, 4.14; Cl, 24.36. Found: C, 65.85; H, 4.22; Cl, 24.44.

EXAMPLE 3

2,3,5,6-DIBENZOBICYCLO[5.1.0]OCTAN-4-OL 8,8-Dichloro-2,3,5,6-dibenzobicyclo[5.1.0]octan-4-ol (2.00 gm., 6.88 mmole), dissolved in 100 ml. of freshly distilled tetrahydrofuran, was placed in a 3-necked flask equipped with a stirrer, dropping funnel, and condenser protected by a drying tube. Lithium wire (0.476 gm., 68.8 mmole) was cut in tiny pieces and immediately added to the reaction mixture. t-Butyl alcohol (5.10 gm., 68.8 mmole) dissolved in 20 ml. of tetrahydrofuran was placed in a dropping funnel and added dropwise to the stirred reaction mixture at room temperature over a 5-hour period. The mixture was stirred overnight at room temperature. Lithium wire (0.476 gm., 68.8 mmole) was cut into tiny pieces and immediately added to the reaction. t-Butyl alcohol (5.10 gm., 68.8 mmole) was added dropwise to the reaction mixture at such a rate that the lithium metal remained reacting. The mixture was again stirred overnight at room temperature. Lithium wire (0.35 gm.) was cut into tiny pieces and immediately added to the reaction. Again, sufficient t-butyl alcohol was added dropwise to consume the lithium metal. The reaction was stirred overnight. The tetrahydrofuran was distilled under reduced pressure from a water bath at 40° C. The residue was taken up in benzene-ether (1:1) and water and transferred to a separatory funnel. The aqueous phase was separated and the organic phase was washed carefully with three 100 ml. portions of water. The combined water extracts were made up to a volume of 500 ml. Analysis of this aqueous solution for chloride ion showed that 95.8% of the chlorine had been removed from the 8,8-dichloro-2,3,5,6-dibenzobicyclo[5.1.0]octan-4-ol. The benzene-ether solution was dried over magnesium sulfate, filtered, and the benzene and ether distilled. The residue was dissolved in 100 ml. of tetrahydrofuran and placed in a 3-necked flask equipped with stirrer, dropping funnel, and condenser protected by a drying tube. Lithium wire (0.30 gm. to 0.39 gm.) and t-butyl alcohol were added as previously described three more times on three consecutive days. The tetrahydrofuran was distilled under reduced pressure from a water bath at 50° C. The residue was taken up in benzene-ether (1:1) and extracted with water. Analysis of the aqueous extracts for chloride ion showed an additional 1.7% of the chlorine had been removed. The benzene-ether solution was dried over magnesium sulfate, filtered, and the benzene and ether distilled under reduced pressure at 50°. The pale tan material was sublimed at 120° and 0.05 mm. to give 0.85 gm. (55.5%) of white crystalline product. An analytical sample was prepared by a second sublimation, m.p. 153°-154.5°. Gas chromatography showed the product to be homogeneous.

Analysis Calc'd. for $C_{16}H_{14}O$: C, 86.45: H, 6.35. Found: C, 86.54; H, 6.27.

EXAMPLE 4

4-CHLORO-2,3,5,6-DIBENZOBICYCLO[5.1.0]OCTANE

4-Hydroxy-2,3,5,6-dibenzobicyclo[5.1.0]octane (1.36 gm., 6.1 mmole) was dissolved in 100 ml. of dry benzene. The solution was cooled in an ice bath and a stream of dry hydrogen chloride was bubbled through the solution for five minutes. Calcium chloride was added to the turbid solution which then was allowed to stand overnight at room temperature. The calcium chloride was removed by filtration and the benzene was removed under reduced pressure (film evaporator) from a bath at 50°. The product, a viscous oil, crystallized on long standing. Recyrstallization from hexane gave 0.74 gm. (50.5%) of hygroscopic product, m.p. 98°-102°. In a subsequent experiment, the oil crystallized easily to give a 73% yield of product.

EXAMPLE 5

2,3,5,6-DIBENZOBICYCLO[5.1.0]OCTAN-4-ONE 2,3,5,6-Dibenzobicyclo[5.1.0]octan-4-ol (0.85 gm., 3.82 mmole) was dissolved in 50 ml. of acetone. The solution was cooled to 0° C. in an ice bath and stirred while a solution of chromium trioxide (1.54 gm., 15.36 mmole) in 13 ml. of concentrated sulfuric acid and 15 ml. of water was added dropwise over a 90 minute period. The green solution was stirred for an additional two hours at 0° to 10° and then acetone was distilled under reduced pressure from a water bath at 0° to 10° C. The mixture was diluted with water (300 ml.) and extracted with two 100 ml. portions of benzene-ether (1:1). The combined benzene-ether extracts were washed with two 25 ml. portions of water, dried over magnesium sulfate, filtered, and the benzene and ether distilled under reduced pressure from a water bath at 70°. The product (0.83 gm.) crystallized on cooling. An analytical sample was prepared by sublimation at 90° and 0.05 mm. The product can be recrystallized from hexane, m.p. 85°-85.6°. The nuclear magnetic resonance spectrum was in accord with the assigned structure.

Analysis Calc'd. for $C_{16}H_{12}O$: C, 87.24; H, 5.49. Found: C, 87.06; H, 5.55.

EXAMPLE 6

PREPARATION OF 4-(3-DIMETHYLAMINOPROPYLIDENE)-2,3,5,6-DIBENZOBICYCLO[5.1.0]OCTANE HYDROGEN MALEATE

A. 8,8-Dichloro-2,3,5,6-dibenzobicyclo[5.1.0]octan-4-ol 8,8-Dichloro-2,3,5,6-dibenzobicyclo[5.1.0]octan-4-one (2.00 gm., 6.93 mole) was dissolved in 40 ml. of hot methanol. The solution was stirred while a solution of 0.941 gm. (17.5 mmole) of potassium borohydride in 10 ml. of water (containing 2 drops of 40% sodium hydroxide solution) was added dropwise over a 15 minute period. The clear solution was refluxed for 1.5 hours. After evaporation of the methanol in vacuo, a white crystalline mass remained. After cooling in an ice bath, the product was collected, washed with water and dried. Recrystallization from aqueous methanol gave product, with m.p. 170.5°-172.5°.

Analysis calc'd. for $C_{16}H_{12}OCl_2$: C, 66.00: H, 4.14; Cl, 24.36. Found: C, 65.85; H, 4.22; Cl, 24.44.

B. 2,3,5,6-Dibenzobicyclo[5.1.0]octan-4-ol 8,8-Dichloro-2,3,5,6-dibenzobicyclo[5.1.0]-octan-4-ol (2.00 gm., 6.88 mmole), dissolved in 100 ml. of freshly distilled tetrahydrofuran, was placed in a 3-necked flask equipped with a stirrer, dropping funnel, and condenser protected by a drying tube. Lithium wire (0.476 gm., 68.8 mmole) was cut in tiny pieces and immediately added to the reaction mixture. t-Butyl alcohol (5.10 gm., 68.8 mmole) dissolved in 20 ml. of tetrahydrofuran was placed in the dropping funnel and added dropwise to the stirred reaction mixture at room temperature over a 5-hour period. The mixture was stirred overnight at room temperature. Lithium wire (0.476 gm., 68.8 mmole) was cut into tiny pieces and immediately added to the reaction. t-Butyl alcohol (5.10 gm., 68.8 mmole) was added dropwise to the reaction mixture at such a rate that the lithium metal remained reacting. The mixture again was stirred overnight at room temperature. Lithium wire (0.35 gm.) was cut into tiny pieces and immediately added to the reaction. Again, sufficient t-butyl alcohol was added dropwise to consume the lithium metal. The reaction was stirred overnight. The tetrahydrofuran was distilled under reduced pressure from a water bath at 40°. The residue was taken up in benzene-ether (1:1) and water and transferred to a separatory funnel. The aqueous phase was separated and the organic phase was washed carefully with three 100 ml. portions of water. The combined water extracts were made up to a volume of 500 ml. Analysis of this aqueous solution for chloride ion showed that 95.8% of the chlorine had been removed from the 8,8-dichloro-2,3,5,6-dibenzobicyclo[5.1.0]-octan-4-ol. The benzene-ether solution was dried over magnesium sulfate, filtered, and the benzene and ether distilled. The residue was dissolved in 100 ml. of tetrahydrofuran and placed in a 3-necked flask equipped with stirrer, dropping funnel, and condenser protected by a drying tube. Lithium wire (0.30 gm. to 0.39 gm.) and t-butyl alcohol were added as previously described three consecutive days. The tetrahydrofuran was distilled under reduced pressure from a water bath at 50° C. The residue was taken up in benzene-ether (1:1) and extracted with water. Analysis of the aqueous extracts for chloride ion showed an additional 1.7% of the chlorine had been removed. The benzene-ether solution was dried over magnesium sulfate, filtered, and the benzene and ether distilled under reduced pressure at 50°. The pale tan material was sublimed at 120° and 0.05 mm. to give a white crystalline product. An analytical sample was prepared by a second sublimation, m.p. 153°–154.5°. Gas chromatography showed the product to be homogeneous.

Analysis calc'd. for $C_{16}H_{14}O$: C, 86.45; H, 6.35. Found: C, 86.54; H, 6.27.

C. 2,3,5,6-Dibenzobicyclo[5.1.0]octan-4-one 2,3,5,6-Dibenzobicyclo[5.1.0]octan-4-ol (0.85 gm., 3.82 mmole) was dissolved in 50 ml. of acetone. The solution was cooled to 0° C. in an ice bath and stirred while a solution of chromium trioxide (1.54 gm., 15.36 mmole) in 13 ml. of concentrated sulfuric acid and 15 ml. of water was added dropwise over a 90-minute period. The green solution was stirred for an additional two hours at 0°–10° and then acetone was distilled under reduced pressure from a water bath at 0° to 10° C. The mixture was diluted with water (300 ml.) and extracted with two 100 ml. portions of benzene-ether (1:1). The combined benzene-ether extracts were washed with two 25 ml. portions of water, dried over magnesium sulfate, filtered and the benzene and ether distilled under reduced pressure from a water bath at 70°. The product crystallized on cooling. An analytical sample was prepared by sublimation at 90° and 0.05 mm. The product can be recrystallized from hexane, m.p. 85°–86.5°. The nuclear magnetic resonance spectrum was in accord with the assigned structure.

Analysis calc'd. for $C_{16}H_{12}O$: C, 87.24; H, 5.49. Found: C, 87.06. H, 5.55.

D. 4-Hydroxy-4-(3-dimethylaminopropyl)-2,3,5,6-dibenzobicyclo[5.1.0]octane 2,3,5,6-Dibenzobicyclo[5.1.0]octan-4-one (0.586 gm., 2.66 mmole), dissolved in 10 ml. of dry tetrahydrofuran was placed in a 3-necked flask equipped with a teflon stirrer, dropping funnel, and condenser protected by a drying tube. An atmosphere of dry nitrogen was maintained in the apparatus during the reaction. The solution was cooled in an ice-water bath and 3-dimethylaminopropyl-magnesium chloride, 10 ml. of a 2.71 M solution in tetrahydrofuran, was added dropwise over a period of 15 minutes. Stirring was continued for 2 hours in the ice-water bath and overnight at room temperature. Gilman's test was positive for Grignard reagent at the end of this time. Tetrahydrofuran was distilled under reduced pressure from a water bath at 30°. The residue was dissolved in benzene, cooled in an ice bath, and the Grignard adduct hydrolyzed by dropwise addition of water until the benzene phase was clear and a stiff gelatinous precipitate remained. The benzene phase was decanted and the gelatinous precipitate was extracted with two 50 ml. portions of hot benzene. The combined benzene extracts were washed with water, dried over magnesium sulfate, filtered, and the benzene evaporated under reduced pressure at 70°. The clear oil crystallized on cooling. Recrystallization from ethanol-water gave analytically pure product, m.p. 137.5°–138.5°.

Analysis calculated for $C_{21}H_{25}ON$: C, 82.04; H, 8.20; N, 4.56. Found: C, 81.91; H, 8.48; N, 4.65.

E. 4-(3-Dimethylaminopropylidene)-2,3,5,6-dibenzobicyclo[5.1.0]octane 4-(3-Dimethylaminopropyl)-4-hydroxy-2,3,5,6-dibenzobicyclo[5.1.0]octane (0.500 gm., 1.63 mmole) was dissolved in a mixture of 5 ml. of trifluoroacetic acid and 5 ml. of trifluoroacetic anhydride. The solution was refluxed for 3 hours and then stirred at room temperature overnight. The trifluoroacetic acid and residual anhydride were evaporated under reduced pressure. The red oil was cooled in an ice bath and rendered alkaline by addition of 10N sodium hydroxide. The product was extracted with benzene, and the benzene phase was washed with two 50 ml. portions of water and dried over magnesium sulfate. After removing the magnesium sulfate by filtration and the benzene by evaporation under reduced pressure (film evaporator) at 70° C., the residual oil was passed over a column of neutral alumina (Merck) 11-inch by ¾-inch packed in benzene. The column was washed with 1 liter of benzene to remove a small nonamine fraction after which the product was eluted with benzene-ether (1:1). Evaporation of the benzene and ether under reduced pressure gave 0.270 gm. of yellow oily base. The base was dissolved in 5 ml. of absolute ethanol and filtered. To this solution was added maleic acid (0.110 gm., 0.95 mmole). The solution was warmed and ether was added to incipient cloudiness. The product melted at 183°–186°. An analytical sample melted at 185°–186.5° after recrystallization from absolute ethanol and ether. The nuclear magnetic resonance spectrum was in accord with the assigned structure.

Analysis calculated for $C_{21}H_{23}N.C_4H_4O_4$: C, 74.05; H, 6.71; N, 3.45. Found: C, 73.98; H, 7.00; N, 3.30.

EXAMPLE 7

PREPARATION OF 4-(3-DIMETHYLAMINOPROPYL)-2,3,5,6-DIBENZOBICYCLO[5.1.0]OCTANE HYDROGEN MALEATE (MIXED ISOMERS)

A. 4-Chloro-2,3,5,6-dibenzobicyclo[5.1.0]octane

4-Hydroxy-2,3,5,6-dibenzobicyclo[5.1.0]octane (1.36 gm., 6.1 mmole) was dissolved in 100 ml. of dry benzene. The solution was cooled in an ice bath and a stream of dry hydrogen chloride was bubbled through the solution for five minutes. Calcium chloride was added to the turbid solution which then was allowed to stand overnight at room temperature. The calcium chloride was removed by filtration and the benzene was removed under reduced pressure from a bath at 50°. The product, a viscous oil, crystallized on long standing. Recrystallization from hexane gave 0.74 gm. (50.5%) of a hygroscopic product, m.p. 98°-102°. In a subsequent experiment, the oil crystallized easily.

B. 4-(3-Dimethylaminopropyl)-2,3,5,6-dibenzobicyclo[5.1.0]octane hydrogen maleate (mixed isomers)

3-Dimethylaminopropylmagnesium chloride, 11 ml. of a 1.6M solution in tetrahydrofuran, was placed in a 25 ml. 3-necked flask that was equipped with a stirrer, reflux condenser, and dropping funnel. An atmosphere of nitrogen was maintained throughout the reaction. The solution was cooled in an ice bath and a solution of 0.736 gm. (3.06 mmole) of 4-chloro-2,3,5,6-dibenzobicyclo[5.1.0]octane in 15 ml. of dry tetrahydrofuran was added over a period of 15 minutes. The solution was stirred one hour at ice bath temperature, 2 hours at room temperature and for 15 minutes at reflux. Gilman's test for Grignard reagent was positive at this time. Tetrahydrofuran was removed by evaporation under reduced pressure from a bath at 23°. The residue was dissolved in benzene (25 ml.), cooled in an ice bath, and the Grignard adduct hydrolyzed by dropwise addition of water until the benzene phase was clear and a stiff gelatinous precipitate formed. The benzene layer was decanted and the residue was extracted with two 25 ml. portions of boiling benzene. The combined benzene extracts were washed with water (50 ml.) and then were extracted with one 35 ml. portion and two 20 ml. portions of 0.5 M citric acid. The combined citric acid extracts were cooled in ice and rendered alkaline by addition of excess 10 N sodium hydroxide. The base that precipitated was extracted into benzene (50 ml.), washed with two 50 ml. portions of water, and dried over magnesium sulfate. Removal of the magnesium sulfate and benzene gave a colorless oil. This oil was passed through a column of acid-washed alumina packed in benzene. The column was washed with 300 ml. of methanol, and the product then was eluted with 150 ml. of water-methanol (1:3). The methanol and water were evaporated under reduced pressure and to the residue was added 50 ml. of benzene, 50 ml. of water and 20 ml. of 10 N sodium hydroxide. The benzene phase was removed, washed with water (3×30 ml.), and dried. Evaporation of the benzene gave an oily product. Nuclear magnetic resonance spectroscopy showed this material to be a mixture of geometric isomers of 4-(3-dimethylaminopropyl)-2,3,5,6-dibenzobicyclo[5.1.0]octane in the approximate ratio of 2 to 1. This base (0.408 gm., 1.4 mmole) was dissolved in 5 ml. of absolute ethanol and 0.170 gm. (1.47 mmole) of maleic acid was added to produce the maleate salt of the base. The solution was warmed, filtered, and 5 ml. of absolute ethanol was added. Ether (40 ml.) was added to incipient cloudiness. The maleate salt was recovered by filtration, m.p. 174°-176° C.

Analysis calculated for $C_{21}H_{25}N \cdot C_4H_4O_4$: C, 73.68; H, 7.17; N, 3.44. Found: C, 73.77; H. 7.28; N, 3.50.

The isomers as the bases can be separated by gas-liquid chromatography.

EXAMPLE 8

PREPARATION OF 4-(3-METHYLAMINOPROPYLIDENE)-2,3,5,6-DIBENZOBICYCLO[5.1.0]OCTANE HYDROGEN MALEATE

A. 4-[3-(N-2-p-tolylsulfonylethoxycarbonyl-N-methylamino)-propylidene]-2,3,5,6-dibenzobicyclo[5.1.0]octane 4-(3-Dimethylaminopropylidene)-2,3,5,6-dibenzobicyclo[5.1.0]octane (2.61 gm., 9.05 mmole) was dissolved in 50 ml. of dry benzene. The solution was stirred magnetically at room temperature while a solution of 2.4 gm. (9.1 mmole) of 2-p-tolylsulfonylethylchloroformate in 15 ml. of benzene was added dropwise over a period of one hour. The solution was refluxed for 12 hours. The precipitate was separated by filtration, washed with benzene, and the combined benzene phases were washed with two 75 ml. portions of water. The benzene phase was washed with three 75 ml. portions of 0.5 M citric acid, water, and dried over magnesium sulfate. Filtration from magnesium sulfate and evaporation of the benzene under reduced pressure at 80° C. gave 3.43 gm. of a light yellow oil. This neutral oil was dissolved in 10 ml. of benzene was passed over a column of silica gel (15-inch by ⅜-inch) packed in benzene. The column was washed with 1 liter of benzene to remove trace impurities, and 4-[3-(N-2-p-tolylsulfonylethoxycarbonyl-N-methylamino)propylidene]-2,3,5,6-dibenzobicyclo[5.1.0]octane was eluted from the column with 200 ml. of methanol. Evaporation of the methanol under reduced pressure at 70° gave a yellow oil, characterized by its infrared spectrum. The material showed a single spot on thin layer chromatography, $R_f 0.34$ (silica gel. 2% isopropyl alcohol in methylene chloride).

B. 4-(3-Methylaminopropylidene)-2,3,5,6-dibenzobicyclo[5.1.0]octane hydrogen maleate A solution of 0.62 gm. (11 mmole) of potassium hydroxide in 15 ml. of absolute methanol was added to 1.10 gm. (2.2 mmole) of 4-[3-(N-2-p-tolylsulfonylethoxycarbonyl-N-methylamino)propylidene]-2,3,5,6-dibenzobicyclo[5.1.0]octane. The mixture was shaken and then allowed to stand for one hour at room temperature. The solution was extracted with 400 ml. of benzene-ether (1:1) after dilution with 125 ml. of water. The benzene-ether phase was extracted with 6 N hydrochloric acid; an oil precipitated. The benzene-ether was decanted and the hydrochloric acid and oil made alkaline by the addition of excess 10 N sodium hydroxide. The alkaline solution was extracted with 200 ml. of benzene. After washing with water, the benzene was extracted with two 100 ml. portions of 0.5 M citric acid. The combined citric acid extracts were washed with benzene and then rendered alkaline by the slow addition of 10 N sodium hydroxide. This alkaline solution was extracted with 100 ml. of benzene and the benzene extract was washed with water (two 100 ml. portions) and dried over magnesium sulfate. Removal of the magnesium sulfate and benzene gave 0.21 gm. (35%) of the viscous oily base. This base was dissolved in 3.5 ml. of absolute ethanol and filtered. To this solution was added 0.094 gm. (0.81 mmole) of maleic acid. The solution was warmed and ether was added to incipient cloudiness. The crude product had m.p. 121°–125° C. Recrystallization from absolute ethanol-ether gave analytically pure material, m.p. 121°–123° C.

Analysis calculated for $C_{20}H_{21}N \cdot C_4H_4O_4$: C, 73.63; H, 6.44; N, 3.58. Found: C, 73.21; H, 6.42; N, 3.67.

What is claimed is:

1. A compound of the formula

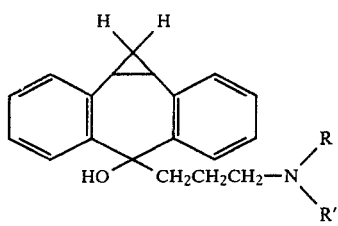

wherein —NRR' is di(lower alkyl) amino.

2. A compound of the formula

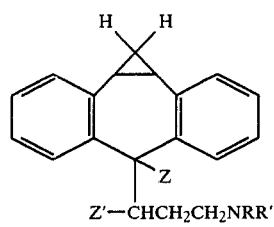

wherein Z and Z' are both hydrogen or Z and Z' together form a bond between the carbon atoms to which they are attached; and —NRR' is selected from the group consisting of (lower alkyl)amino and di(lower alkyl)amino.

3. A compound of the formula

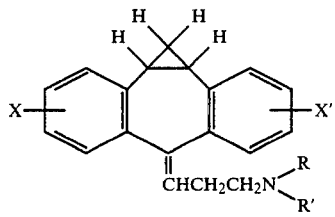

wherein
R is lower alkyl, and
R' is either hydrogen or lower alkyl; and
X and X' are hydrogen.

4. The compound in accordance with claim 3 wherein X and X' are hydrogen and R and R' are lower alkyl.

5. The compound in accordance with claim 3 wherein X and X' are hydrogen and R and R' are methyl.

6. A compound of the formula

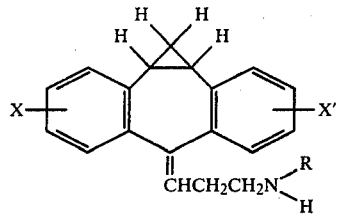

wherein X, X' and R are as defined in claim 3.

7. The compound in accordance with claim 6 wherein X and X' are hydrogen, and R is lower alkyl.

8. A compound according to claim 6 wherein X and X' are hydrogen and R is methyl.

9. A compound of the formula

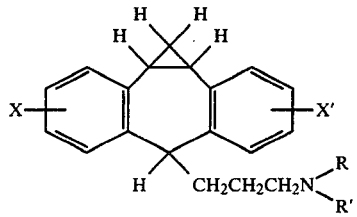

wherein X and X', R and R' are as defined in claim 3.

10. A compound in accordance with claim 9 wherein X and X' are hydrogen, and R and R' are lower alkyl.

11. A compound in accordance with claim 9 wherein X and X' are hydrogen, R and R' are methyl.

12. A compound of the formula

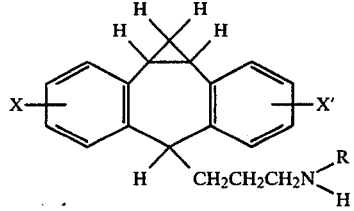

wherein X, X' are R are as defined in claim 3.

13. A compound in accordance with claim 12 wherein X and X' are hydrogen and R is lower alkyl.

14. A compound in accordance with claim 12 wherein X and X' are hydrogen and R is methyl.

15. A compound of the formula

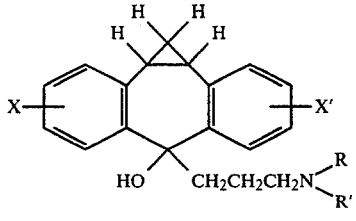

wherein X, X', R and R' are as defined in claim 3.

16. A compound in accordance with claim 15 wherein X and X' are hydrogen and R and R' are methyl.

* * * * *